United States Patent
Hedges et al.

(10) Patent No.: US 6,187,016 B1
(45) Date of Patent: Feb. 13, 2001

(54) STENT RETRIEVAL DEVICE

(76) Inventors: Daniel G. Hedges, 4015 Beautyrose Ave., Westerville, OH (US) 43081; Barry S. George, 6045 St. Boswels Ct., Dublin, OH (US) 43017

(*) Notice: Under 35 U.S.C. 154(b), the term of this patent shall be extended for 0 days.

(21) Appl. No.: 09/395,116

(22) Filed: Sep. 14, 1999

(51) Int. Cl.⁷ .................................................. A61F 11/00
(52) U.S. Cl. ......................... 606/108; 606/191; 606/192; 606/194
(58) Field of Search ........................... 606/108, 194, 606/191, 192, 195, 198, 113; 604/96, 104; 623/1.11, 11.11, 12.11

(56) References Cited

U.S. PATENT DOCUMENTS

| | | | |
|---|---|---|---|
| 4,990,151 | 2/1991 | Wallsten | 606/108 |
| 5,098,440 | * 3/1992 | Hillstead | 606/108 |
| 5,464,408 | * 11/1995 | Duc | 606/108 |
| 5,474,563 | * 12/1995 | Myler et al. | 606/108 |
| 5,520,697 | 5/1996 | Lindenberg et al. | 606/108 |
| 5,624,450 | * 4/1997 | Glastra | 606/108 |
| 5,910,144 | * 6/1999 | Hayashi | 606/108 |
| 6,027,508 | * 2/2000 | Ren et al. | 606/108 |
| 6,027,509 | * 2/2000 | Schatz et al. | 606/108 |

* cited by examiner

*Primary Examiner*—Pedro Philogene
(74) *Attorney, Agent, or Firm*—John L. Gray, Esq.; Kegler, Brown, Hill & Ritter

(57) ABSTRACT

A stent retrieval device for insertion in an artery and capable of being guided along a radiopaque wire is described. The stent retrieval device includes a plurality of flexible individual fingers housed in a flexible tube with the fingers normally biased toward the interior surface of the tube so that when they are pushed out of the tube they will expand the artery and then grasp the stent to be removed.

4 Claims, 3 Drawing Sheets

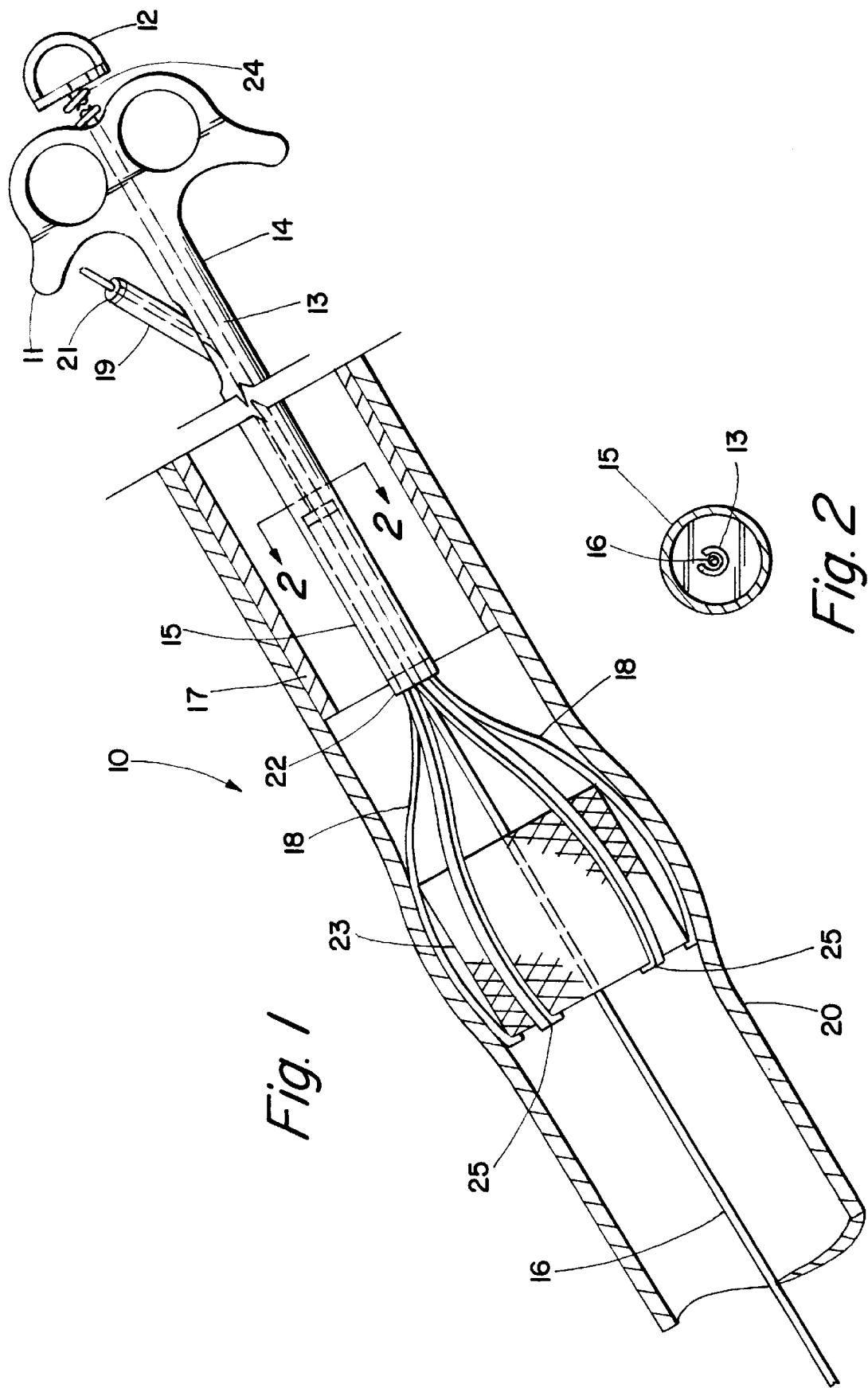

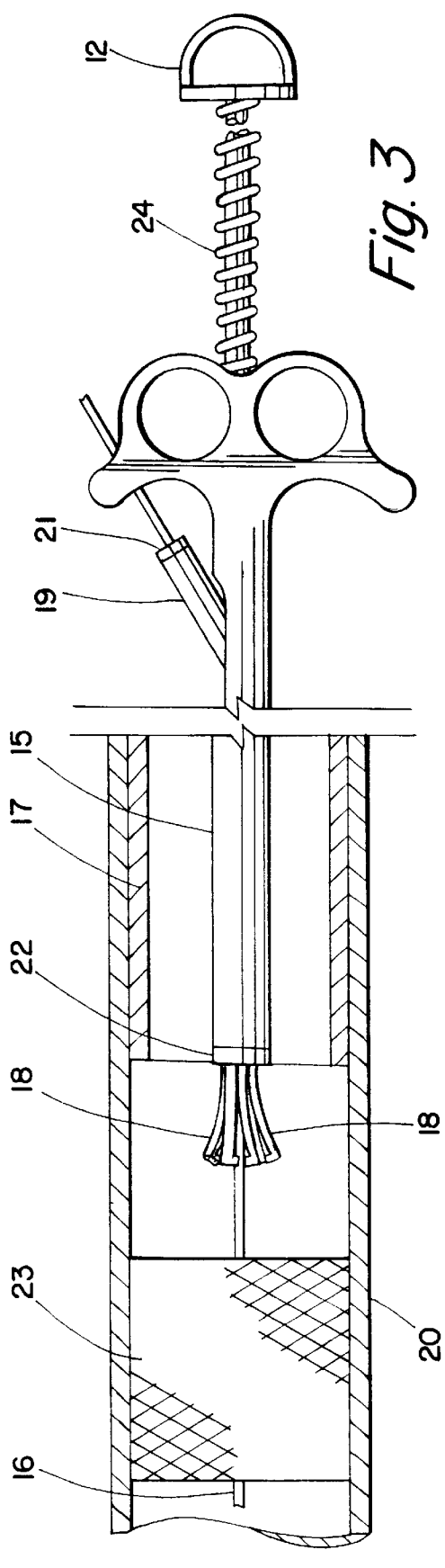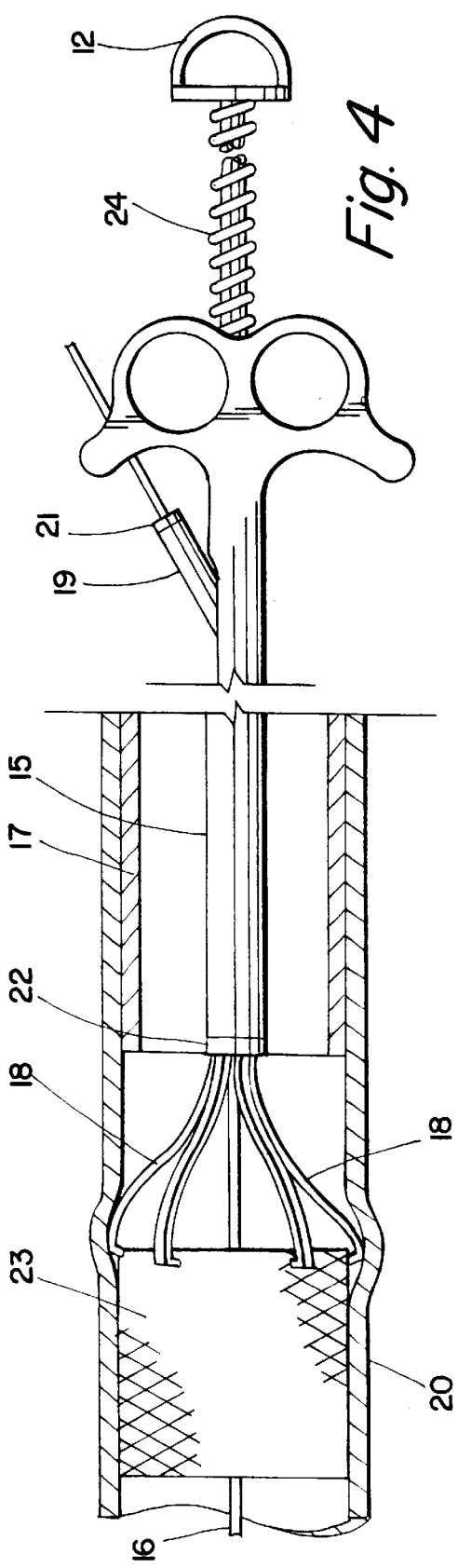

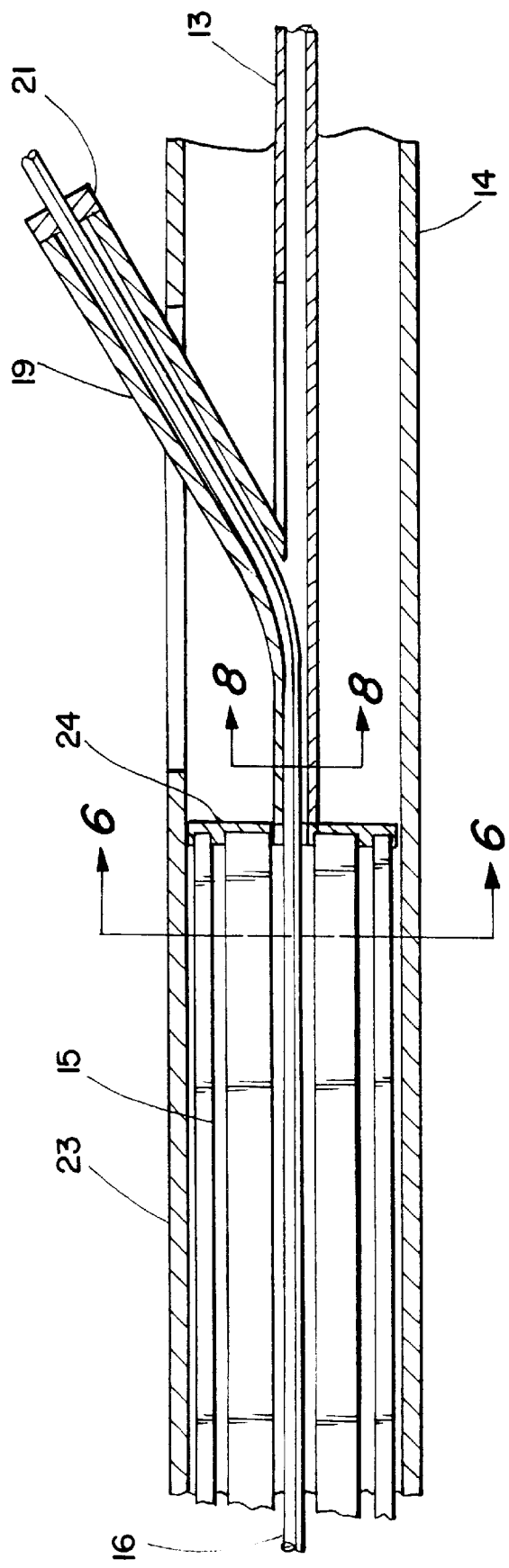
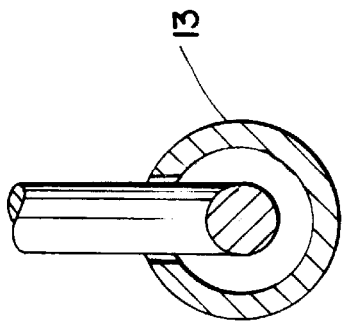
Fig. 7
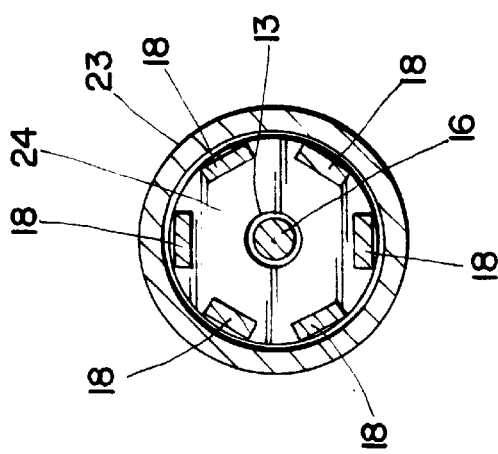
Fig. 5
Fig. 6

STENT RETRIEVAL DEVICE

BACKGROUND OF THE INVENTION

Often times following balloon angioplasty, it is necessary to insert a coronary stent into the artery to keep the artery open. On occasion it is necessary to remove the stent from the artery. There are a number of devices that have been proposed for this purpose. One is shown in U.S. Pat. No. 5,098,440 Hillstead which is a loop device for engaging the stent and removing it. Another is U.S. Pat. No. 5,464,408 Duc which utilizes two flexible tubes with a number of gripping members which are part of the inner tube which are directed to engage the stent and pull it into the outer tube. U.S. Pat. No. 4,990,151 Wallsten shows a stent removal device where the portion which engages the stent is straight and would not expand the artery to permit the stent to be drawn back more easily.

In balloon angioplasty, a small radiopaque guidewire is steered through a coronary guiding catheter and down a coronary artery past the area of blockage and over the wire. The physician then passes a thin flexible tube with a balloon at the end of it into the blocked artery. By inflating the balloon, the plaque causing the blockage is pressed back against the artery wall. Doing this, of course, opens the artery and increases the blood flow through the artery to the heart muscle. When the coronary stent is introduced into the blood vessel, it is collapsed down upon the balloon catheter until it reaches the narrow area of the artery. Sometimes, however, the stent may slip back off the balloon or become dislodged in the placement process and must be retrieved.

BRIEF SUMMARY OF THE INVENTION

The invention involves a stent retrieval device which may be guided along the radiopaque guidewire to the location where the stent is to be removed at which time the fingers of the device are pushed out of the tube in which they have been carried. They are naturally biased outward so that they will expand the artery and go over the stent and then grip it as the fingers are drawn back thus keeping the artery expanded and enabling the stent to be readily withdrawn from its location in the artery.

It is therefore an object of this invention to provide a stent removal device which may be inserted into an artery and grip a stent by enveloping it between the stent and the interior artery wall, and thus grasp it and remove it.

It is a further object of this invention to provide such a stent removal device that may be guided along the radiopaque guidewire.

This, together with other objects of the invention, will become apparent from the following detailed description of the invention and the accompanying drawings.

BRIEF DESCRIPTION OF THE DRAWINGS

FIG. 1 is a perspective view, partly in section, showing applicant's invention in use in grasping a stent inside of an artery.

FIG. 2 is a section of FIG. 1 in the plane 2—2.

FIG. 3 is a side elevation of applicant's invention, partly in section, showing its movement through artery along the radiopaque guidewire.

FIG. 4 is a view of applicant's invention with the fingers expanded and commencing to expand the artery and grasp the stent.

FIG. 5 is a sectional view of a portion of applicant's invention showing the provision for guiding the radiopaque guidewire out of applicant's invention.

FIG. 6 is a section of FIG. 5 in the plane 6—6.

FIG. 7 is a section of FIG. 5 in the plane 7—7.

DETAILED DESCRIPTION OF THE INVENTION

Referring now to FIG. 1, applicant's invention is shown generally at 10 and consists of a handle 11, a spring loaded member 12 which is attached to a hollow rod 13 which is located inside of the major shaft 14 and which in turn is connected to flexible tube 15 surrounding the radiopaque guidewire 16 inside the flexible guiding catheter 17. The end of the hollow rod 13 is connected to a base 17a supporting a plurality of fingers 18—18 which are spaced around the inner circumference of the tube 15. The tube 14 is provided with a channel portion 14a to permit the rod 13 to be moved in our out of the artery and also to permit connecting shaft 19 to move accordingly. The fingers 18—18 are normally in a retracted position in flexible tube 15 as this flexible tube moves along the radiopaque guidewire 16 through the artery 20. A radiopaque marker 22 is provided at the end of the flexible tube 15 so as to enable the physician to locate the end of flexible tube 15 prior to opening the fingers 18—18. The guidewire 16 is led out of the flexible tube 15 by means of the shaft 19 which may be provided with a conventional lure lock 21 which is used for flushing tube 15 prior to insertion. All of this activity, of course, is being observed by means of a fluoroscope on the part of the operator of the device and when the flexible tube 15 nears the stent 23, the fingers 18—18 are pushed forward out of the flexible tube 15 by means of the spring loaded member 12, normally biased outward by spring 24, and the fingers 18—18 will expand the interior of the artery 20 and encompass the stent 23. The ends of the fingers 18—18 are preferably bent inwardly as shown at 25—25 to more readily grasp the stent 23.

As shown at FIG. 2, it will be seen that the rod 13 is U-shaped in cross section so that the radiopaque guidewire 16 will fit inside of it.

Referring now to FIG. 3, the fingers 18—18 are just now beginning to emerge from the flexible tube 15 by applying slight pressure on the spring loaded member 12 against spring 24.

Referring now to FIG. 4, further pressure has been applied to spring loaded member 12 and the fingers 18—18 have further expanded since they are normally biased outwardly and are beginning to expand and push out the interior of the artery 20 so as to grasp stent 23. When the stent 23 has been grasped as shown in FIG. 1, then the entire unit including the flexible guiding catheter 17 and the flexible tube 15 may be removed from the artery along with the stent 23 and eventually, of course, the radiopaque guidewire 16 is also removed.

FIG. 5 is a sectional view of applicant's invention showing the radiopaque guidewire 16 traveling in the rod 13 which as shown in FIG. 2 is U-shaped in cross section to accommodate the radiopaque guidewire 16 where it is positioned in the rod 13.

FIG. 6 is a sectional view showing where rod 13 joins round base 17a to which the fingers 18—18 are attached.

FIG. 7 is a section along the plane 7—7 showing the radiopaque wire 16 entering the U-shaped portion of rod 13.

In operation with the radiopaque guidewire 16 in place in the artery 20, the radiopaque guidewire 16 is threaded through the flexible tube 15 and the hollow rod 13 and out the slot 19. The flexible tube 15 is then inserted through the flexible guiding catheter 17 until the area of the stent 23 is located. During this time the fingers 18—18 are retracted into the flexible tube 15. When the flexible tube 15 approaches the stent 23, the spring loaded member 12 is pressed in and the fingers 18—18 which are biased outwardly are pushed out and expand as shown in FIG. 4 and commence to enlarge the interior walls of the artery 20 until they embrace the stent 23 and then the pressure on the spring loaded member 12 is partially relieved permitting the fingers 16 to be drawn slightly back toward the flexible tube 15. Then the entire stent 23 with fingers 18—18 grasping the stent 23, and the flexible tube 15 and the flexible guiding catheter 17 are withdrawn along the radiopaque guidewire 16 to the exterior of the artery 20.

In using this device for stent removal, great reliability is achieved.

While this device is shown for use in the coronary arteries, it can also be used in the periphery vessels in the arms and legs and also in the operating room during laparoscopy.

While this invention has been shown and described with respect to a detailed embodiment thereof, it will be understood by those skilled in the art that various changes in form and detail thereof may be made without departing from the scope of the claims of the invention.

What is claimed is:

1. A stent retrieval device comprising:

a single flexible tube having a central axis and an open end, a plurality of flexible individual fingers in said tube and spaced around the inner circumference of said tube and extending in a direction parallel to the central axis of said tube, the portion of said flexible individual members spaced from the ends thereof being normally biased toward the interior surface of said tube and terminating in ends projecting toward the central axis of said tube which are not biased to the same extent, so that when said flexible individual members are extended out of the tube the portion of said flexible individual members spaced from the ends thereof will expand further than the ends thereof thereby permitting said ends projecting toward the central axis of said tube to pass over the stent being retrieved but then grasp said stent when they reach the end thereof, means for moving said flexible individual members in a direction along the central axis of said tube, said means for moving said flexible individual members being actuated by means exterior of said tube.

2. The stent retrieval device of claim 1 wherein said flexible tube may surround a radiopaque guidewire.

3. The stent retrieval device of claim 1 where said open end of said tube is provided with a radiopaque marker.

4. The stent retrieval device of claim 1 wherein said means for moving said flexible individual members in a direction along the central axis of said tube includes means to receive said guidewire.

* * * * *